(12) United States Patent
Lauf et al.

(10) Patent No.: US 10,849,763 B2
(45) Date of Patent: Dec. 1, 2020

(54) LATERAL SPINE PLATE WITH COLLAPSIBLE VERTEBRAL ATTACHMENT ARMS

(71) Applicant: Life Spine, Inc., Huntley, IL (US)

(72) Inventors: Garrett D. Lauf, Hampshire, IL (US); Daniel P. Predick, West Lafayette, IN (US)

(73) Assignee: LIFE SPINE, INC., Huntley, IL (US)

( * ) Notice: Subject to any disclaimer, the term of this patent is extended or adjusted under 35 U.S.C. 154(b) by 23 days.

(21) Appl. No.: 15/958,278

(22) Filed: Apr. 20, 2018

(65) Prior Publication Data

US 2018/0303629 A1    Oct. 25, 2018

Related U.S. Application Data

(60) Provisional application No. 62/487,699, filed on Apr. 20, 2017.

(51) Int. Cl.
| | | |
|---|---|---|
| *A61F 2/44* | (2006.01) | |
| *A61B 17/58* | (2006.01) | |
| *A61B 17/70* | (2006.01) | |
| *A61B 17/86* | (2006.01) | |
| *A61B 17/80* | (2006.01) | |
| *A61F 2/30* | (2006.01) | |

(52) U.S. Cl.
CPC ............ *A61F 2/4455* (2013.01); *A61B 17/70* (2013.01); *A61B 17/7059* (2013.01); *A61B 17/8605* (2013.01); *A61B 17/80* (2013.01); *A61F 2/442* (2013.01); *A61F 2002/305* (2013.01); *A61F 2002/30433* (2013.01); *A61F 2002/30471* (2013.01); *A61F 2002/30578* (2013.01)

(58) Field of Classification Search
CPC ................... A61F 2/442; A61F 2/4455; A61F 2002/30433; A61F 2002/30477; A61F 2002/30471; A61F 2002/305; A61F 2002/30578; A61F 2002/30329; A61F 2002/30331; A61B 17/70; A61B 17/7059; A61B 17/8605; A61B 17/80
USPC ........ 606/70–71, 280–299; 623/17.11–17.16
See application file for complete search history.

(56) References Cited

U.S. PATENT DOCUMENTS

| | | | | |
|---|---|---|---|---|
| 8,343,223 | B2 * | 1/2013 | Bucci | A61F 2/4455 623/17.16 |
| 8,852,278 | B2 * | 10/2014 | Bellas | A61F 2/447 623/17.11 |
| 2008/0177390 | A1 * | 7/2008 | Mitchell | A61F 2/4425 623/17.16 |

(Continued)

*Primary Examiner* — Jessica Weiss
(74) *Attorney, Agent, or Firm* — Foley & Lardner LLP

(57) ABSTRACT

A lateral spine implant has a lateral spine cage and an associated lateral spine plate with one or more folding vertebral attachment arms, each arm configured for attachment to vertebral bone. The ability of the one or more arms to fold allows the lateral spine plate to be inserted/implanted at a lower profile height than traditional lateral spine plates. The lateral spine plate is meant to be used at times of intended or unintended compromise of the anterior longitudinal ligament (ALL) to prevent interbody cage migration, but may be adapted for any lateral plating application. Once expanded, each attachment arm is configured to receive a bone screw for securing the attachment arm to a vertebra, the bone screw retained by rotating cam lock nuts of the attachment arm.

9 Claims, 12 Drawing Sheets

(56) References Cited

U.S. PATENT DOCUMENTS

| | | | | |
|---|---|---|---|---|
| 2008/0183294 A1* | 7/2008 | Adl | ............... | A61F 2/442 |
| | | | | 623/17.16 |
| 2008/0294262 A1* | 11/2008 | Levieux | ............... | A61F 2/4611 |
| | | | | 623/17.16 |
| 2010/0030334 A1* | 2/2010 | Molz, IV | ............... | A61F 2/4611 |
| | | | | 623/17.11 |
| 2010/0249937 A1* | 9/2010 | Blain | ............... | A61F 2/447 |
| | | | | 623/17.16 |
| 2011/0015745 A1* | 1/2011 | Bucci | ............... | A61F 2/4455 |
| | | | | 623/17.16 |
| 2011/0224793 A1* | 9/2011 | Fortin | ............... | A61F 2/44 |
| | | | | 623/17.12 |
| 2013/0060288 A1* | 3/2013 | Rodgers | ............... | A61B 17/1604 |
| | | | | 606/281 |
| 2013/0166027 A1* | 6/2013 | Bellas | ............... | A61F 2/447 |
| | | | | 623/17.16 |
| 2013/0345813 A1* | 12/2013 | Frank | ............... | A61B 17/7059 |
| | | | | 623/17.16 |
| 2015/0297356 A1* | 10/2015 | Gamache | ............... | A61F 2/442 |
| | | | | 623/17.16 |
| 2016/0000486 A1* | 1/2016 | Leduc | ............... | A61B 17/8095 |
| | | | | 606/297 |
| 2016/0058481 A1* | 3/2016 | Blain | ............... | A61B 17/8047 |
| | | | | 606/279 |
| 2016/0213481 A1* | 7/2016 | Blain | ............... | A61F 2/4405 |

* cited by examiner

LATERAL SPINE PLATE WITH COLLAPSIBLE VERTEBRAL ATTACHMENT ARMS

CROSS-REFERENCE TO RELATED APPLICATIONS

This U.S. non-provisional patent application claims the benefit of and/or priority under 35 U.S.C. § 119(e) to U.S. provisional patent application Ser. No. 62/487,699 filed Apr. 20, 2017 titled "Lateral Spine Plates With Collapsible Vertebral Attachment Arms," the entire contents of which is specifically incorporated herein by reference.

FIELD OF THE INVENTION

The present invention relates to orthopedic implants such as cages, plates, and screws for the spine and, more particularly to lateral spine cages having vertebral attachment capabilities.

BACKGROUND OF THE INVENTION

People contend with spine issues as a result of age, disease, trauma, and congenital and acquired complications and conditions. While some of these issues can be alleviated without surgery, other issues respond better to surgery. In some cases, such as vertebral fusion, surgery includes installing one or more orthopedic implants.

One type of orthopedic implant used in spinal fusion surgery is an interbody cage. The interbody cage is received in the disc space between adjacent vertebrae in order to facilitate and/or promote fusion between the adjacent vertebrae. Various interbody spine cages have been developed over the years. There are interbody cages for anterior introduction and placement into a disc space of the spine (AIF or Anterior Interbody Fusion), interbody cages for posterior introduction and placement into the disc space of the spine (PIF or Posterior Interbody Fusion), and interbody cages for lateral introduction and placement into the disc space of the spine (LIF or Lateral Interbody Fusion). Interbody cages are also attachable to a vertebra by one or more bone screws in order to inhibit and/or prevent the cage from moving after implantation.

As in most surgeries, one aim is to reduce trauma at the surgical site. To this end surgical procedures such as minimally invasive techniques are now used extensively. Orthopedic implants are often part of or a main goal of surgery. The size of an orthopedic implant has a bearing on the amount of trauma sustained at the implant site. Generally, the smaller the implant, the less trauma at the surgical site. It is therefore an object to provide an orthopedic implant that is minimal in size.

With laterally inserted spinal interbody cages, a spine plate may be used that allows attachment of the spine plate to a lateral side of a vertebra while the spinal interbody cage rests in the disc space. The lateral spine plate thus extends generally perpendicular to the longitudinal axis of the spinal interbody cage. The lateral spine plate spans the disc space along a lateral side(s) of the vertebra(e) and overlays a portion of either an upper or lower vertebra, or a portion of both an upper and lower vertebra in order to attach the lateral spine plate to the lateral side(s) of the vertebra(e) via bone screws. Such lateral spine plates are generally large and thus have a large profile, thereby increasing the chance of surgical trauma. It is apparent that it would be desirable to have a low profile lateral spine plate for a lateral interbody spine cage in order to reduce surgical trauma.

It is an object of the present invention to provide a lateral spine plate for a lateral interbody spine cage having a low surgical profile. It is further an object of the present invention to provide a lateral spine plate for a lateral interbody spine cage that overcomes the deficiencies of the prior art.

SUMMARY OF THE INVENTION

A lateral spine plate for a lateral spinal interbody cage has one or more collapsible/folding arms configured for attachment to one or more vertebrae, the ability of the one or more arms to collapse/fold allows the lateral spine plate to be inserted/implanted at a lower profile height than traditional lateral spine plates. The lateral spine plate is also modular respective to a standard spinal interbody cage allowing securement to the interbody cage when needed.

The present lateral spine plate is meant to be used at times of intended or unintended compromise of the anterior longitudinal ligament (ALL) to prevent interbody cage migration, but may be adapted for any lateral plating application.

Once expanded, each attachment arm is configured to receive a bone screw for securing the attachment arm to a vertebra, the bone screw retained by rotating cam lock nuts of the attachment arm.

The lateral spine plate has a hub with the one or two attachment arms each one pivotally connected to the hub. The hub has a bore that receives a pin for attaching the hub (plate) to the interbody cage.

In one form, the attachment pin has a compressible arrow tip that compresses within an insertion hole of the interbody cage and, upon reaching an inner wall of a window of the interbody cage, will expand and prevent disassociation. In one form, the shaft of the attachment pin includes threads that mate with threads of the insertion hole of the interbody cage to provide additional engagement with the interbody cage. The length of the attachment pin compressible arrow tip and threads provide the ability to adjust offset distance of the lateral spine plate from the interbody cage to allow for preferred placement of the interbody cage within the disc space and/or due to anatomical variations (e.g. osteophytes) that require accommodation.

In one form, the attachment pin has a threaded shaft for engaging the threads of the insertion hole of the interbody cage, but is sans a compressible arrow tip. Other variations are contemplated.

The central hub of the lateral spine plate preferably, but not necessarily, has a slot that receives the attachment pin and allows the threaded shaft thereof to translate anterior/posterior so that position of the lateral spine plate is not entirely dictated by placement of the interbody cage.

The central hub of the lateral spine plate may be configured to receive the attachment pin such that the threaded shaft thereof can translate in the cephalad/caudal direction in order to accommodate varying heights of the selected cage.

In one form, the collapsible/folding vertebral attachment arm is comprised of two translating members (in the cephalad/caudal direction) allowing the ability to accommodate varying heights of the interbody cage.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate forms of the present invention, wherein.

DETAILED DESCRIPTION OF THE INVENTION

Figure 1:
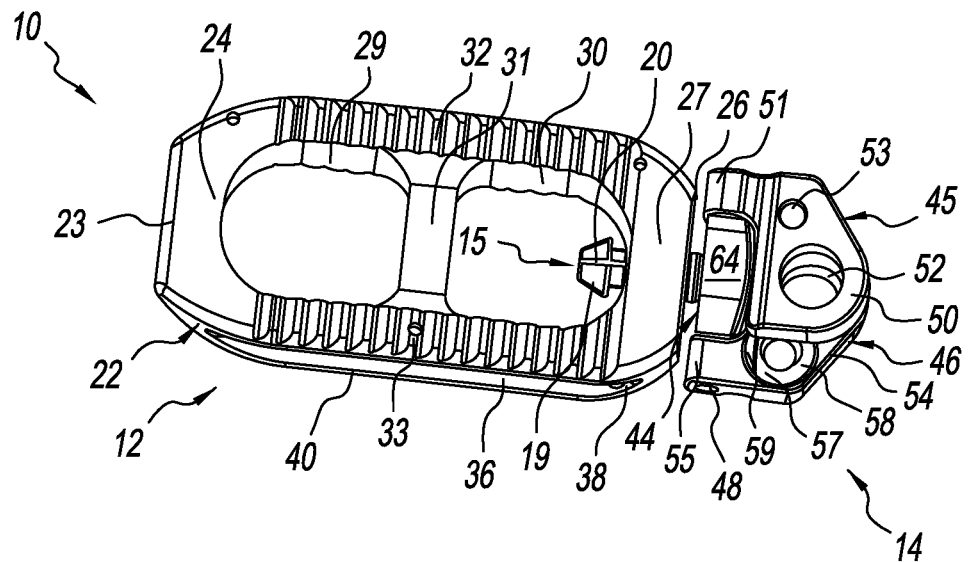
FIG. 1 is an isometric view of a lateral spinal interbody cage with a lateral spine plate having collapsible vertebral attachment arms fashioned in accordance with the principles of the present invention, the vertebral attachment arms in a collapsed or folded position.

Referring to FIGS. 1-7, there is depicted an exemplary form of a lateral spine plate, generally designated 14, adapted/configured to be connected, attached, or coupled to a lateral interbody spine cage, generally designated 12. Together, the lateral interbody spine cage 12 and the lateral spine plate 14 is a lateral spinal implant, generally designated 10. The lateral spinal implant 10 is made from a biocompatible material such as, but not limited to, titanium, stainless steel, or an alloy of titanium or steel. Other biocompatible materials may be used and are contemplated. The lateral spine plate implant 10 may be used for any portion of the spine.

The lateral spine plate 14 may be used generally with all types of lateral interbody spine cages not just with the lateral interbody spine cages shown and/or described herein. The lateral interbody spine cage 14 of the lateral spinal implant 10 is characterized by a generally rectangular body 22 defining a first end or nose 23 and a second end or rear 26, the nomenclature first and second being arbitrary. The nose 23 is inserted first into the interbody cavity/space during implantation and thus has a general curvature defining an upper (superior) curved surface 24 and a lower (inferior) curved surface 25. The rear 26 is generally planar having a slightly slanted upper (superior) surface 27 and a slightly slanted lower (inferior) surface 28. A first opening 29 is situated proximate the nose 23 while a second opening 30 is situated proximate the rear 26, the first and second openings 29, 30 separated by a bridge 31, the nomenclature first and second being arbitrary.

Figure 9:
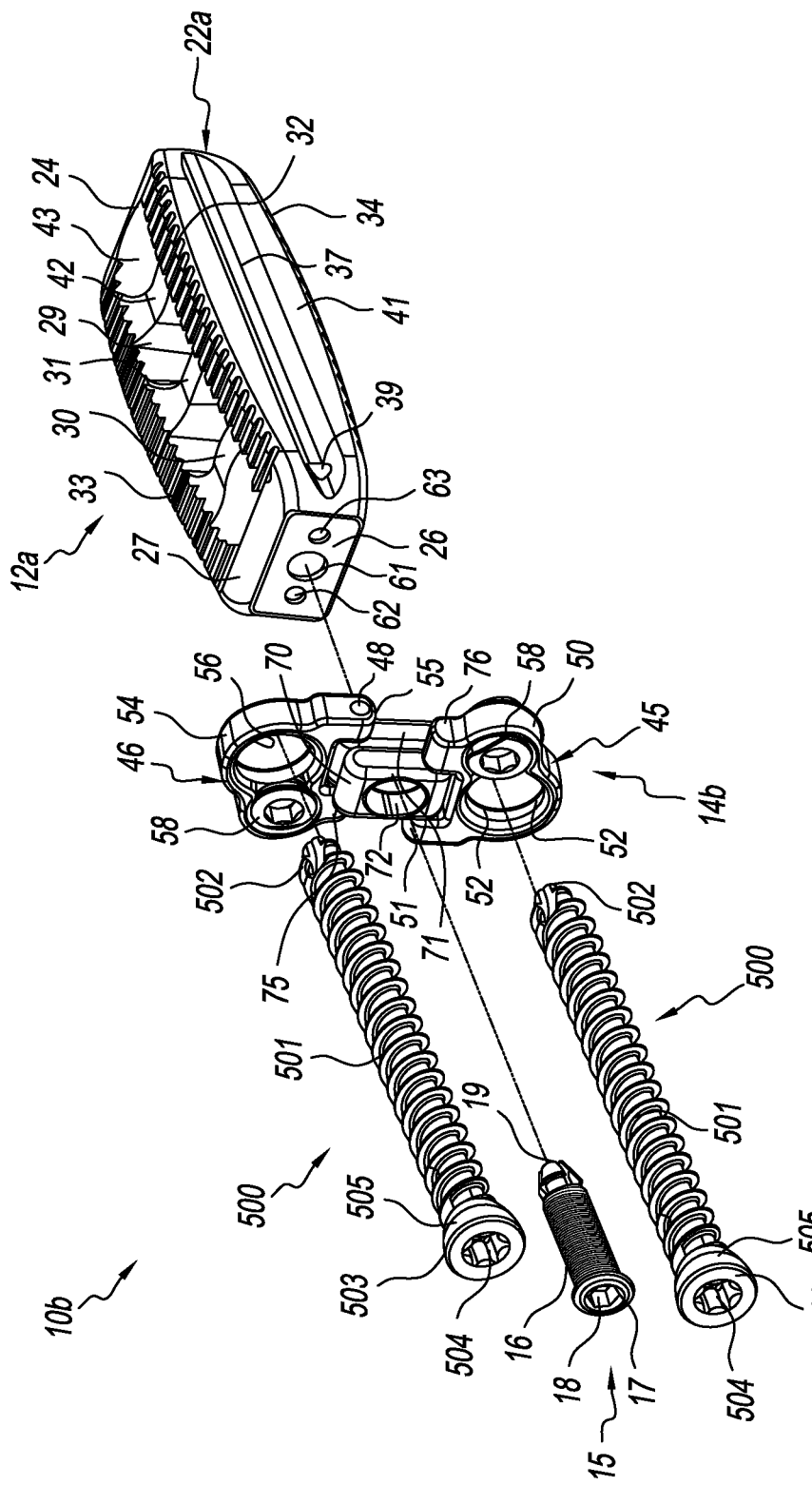
FIG. 9 is an exploded isometric view of another lateral spinal interbody cage with a lateral spine plate having collapsible vertebral attachment arms fashioned in accordance with the principles of the present invention, the vertebral attachment arms in an expanded or open position receiving bone screws and an attachment pin.

The body 22 and the first and second openings 29, 30 define a first upper (superior) side surface 32 having serrations, teeth or the like along its length, and a second upper (superior) side surface 33 having serrations, teeth or the like along its length, the nomenclature first and second being arbitrary. The body 22 and the first and second openings 29, 30 define a first lower (inferior) side surface 34 having serrations, teeth or the like along its length, and a second lower (inferior) side surface 35 having serrations, teeth or the like along its length, the nomenclature first and second being arbitrary. The body 22 further defines a first lateral side 40 having a longitudinal channel or groove 36 and a second lateral side 41 likewise having a longitudinal channel or groove 37, the nomenclature first and second being arbitrary. A bore opening 38 is provided in the first lateral side 40 proximate the rear 26 while a bore opening 39 is provided in the second lateral side 41 proximate the rear 26. As seen in FIG. 9 with respect to a spinal interbody cage variation 12a of the spinal interbody cage 12, but applicable to the spinal interbody cage 12, the rear 26 has an insertion hole 61 that is preferably, but not necessarily, be threaded. The rear 26 may also have first and second lateral holes 62, 63 (with the nomenclature first and second being arbitrary) on each side of the insertion hole 61, the first and second lateral holes 62, 63 being preferably, but not necessarily, smaller than the insertion hole 61. Thus describes a typical lateral interbody spine cage to which the present lateral spine plate 14 may be attached. The lateral spine plate 14 may be attached to other lateral interbody spine cages such as shown and/or described herein, or otherwise.

Figure 2:
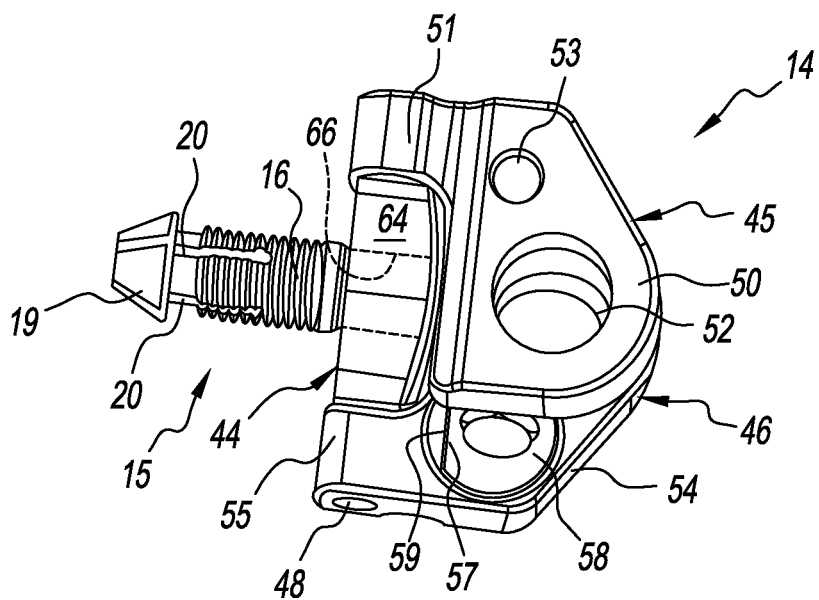
FIG. 2 is an isometric view of the lateral spine plate of FIG. 1 with its vertebral attachment arms in the collapsed or folded position.
Figure 3:
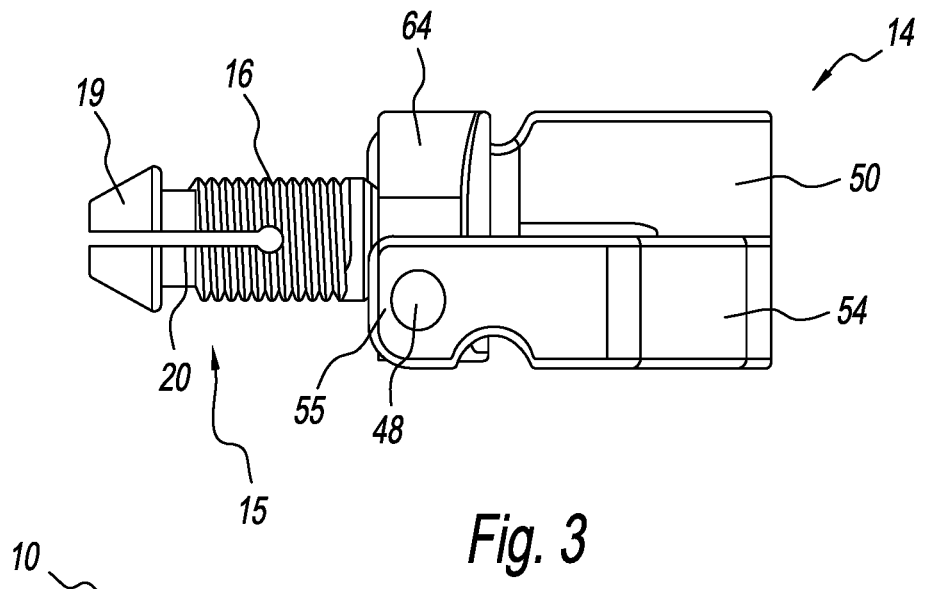
FIG. 3 is a side view of the lateral spine plate of FIG. 1 with its vertebral attachment arms in the collapsed or folded position.
Figure 4:
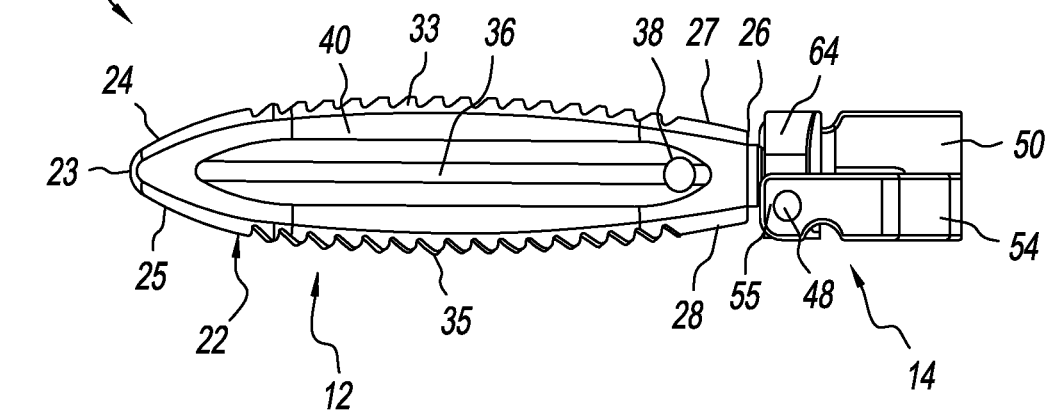
FIG. 4 is a side view of the lateral spinal interbody cage and lateral spine plate of FIG. 1 with the vertebral attachment arms of the lateral spine plate in the collapsed or folded position.
Figure 5:
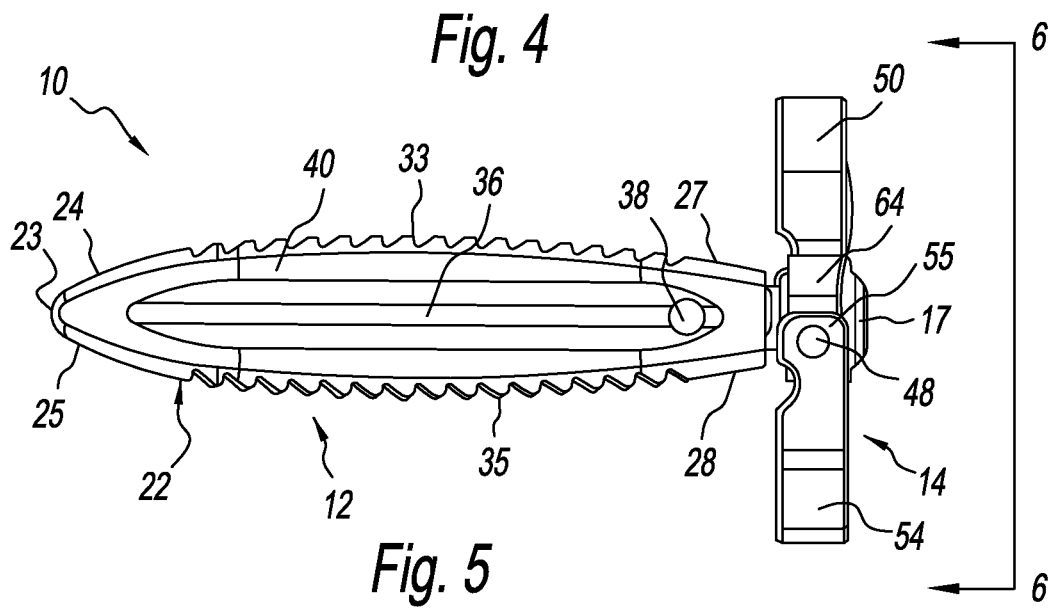
FIG. 5 is a side view of the lateral spinal interbody cage and lateral spine plate of FIG. 1 with the vertebral attachment arms of the lateral spine plate in an expanded or open position.

The lateral spine plate 14 has a central hub 44 defined by a generally rectangular body 64 having a bore 66 extending through the body 64 (see FIG. 2). The lateral spine plate 14 has a first, upper or superior vertebral attachment arm 45 and a second, lower or inferior vertebral attachment arm 46, the nomenclature first and second being arbitrary, each one configured for securement (attachment) to a vertebra via a bone screw 500. The first vertebral attachment arm 45 is defined by a body 50 having a bone screw bore 52 configured to accept and hold a bone screw 500, and a lock nut bore 53 with a lock nut 58. The body 50 further has a boss 51 at a rear side thereof that is pivotally connected to a side of the hub 44 via a hinge (not seen) such that the first attachment arm 45 can pivot or swing from or into a collapsed or folded position (e.g., FIGS. 1-4) to or from an expanded or open position (e.g. FIGS. 5-7). The second vertebral attachment arm 46 is defined by a body 54 having a bone screw bore 56 configured to accept and hold a bone screw 500, and a lock nut bore 57 with a lock nut 58. The body 54 further has a boss 55 at a rear side thereof that is pivotally connected to a side of the hub 44 via a hinge 48 such that the second attachment arm 46 can pivot or swing from or into a collapsed or folded position (e.g., FIGS. 1-4) to or from an expanded or open position (e.g. FIGS. 5-7). In this manner, the lateral spine plate 14 may be implanted in a collapsed or folded position to provide a low profile, then expanded or opened for attachment to the vertebrae.

The lateral spine plate 14 is connected to the lateral interbody cage 12 via an attachment pin 15. In one form, the attachment pin 15 has a threaded shaft 16, a head 17 with a configured socket 18, and an arrow tip 19. Slots 20 are formed in the tip 19 and through a portion of the threaded shaft 16 to provide compressibility of the arrow tip 19. The compressible arrow tip 19 compresses within the insertion hole 60 of the lateral interbody spine cage 12 and, upon reaching an inner wall of the opening 30 of the lateral interbody spine cage, expands and prevents disassociation (see FIG. 1). The threaded shaft 16 of the attachment pin 15 mate with threads of the insertion hole 60 of the lateral interbody spine cage 12 to provide additional engagement with the lateral interbody spine cage 12. The length of the attachment pin 15 provides the ability to adjust offset distance of the lateral spine plate from the interbody cage to allow for preferred placement of the interbody cage within the disc space and/or due to anatomical variations (e.g. osteophytes) that require accommodation.

Figure 6:
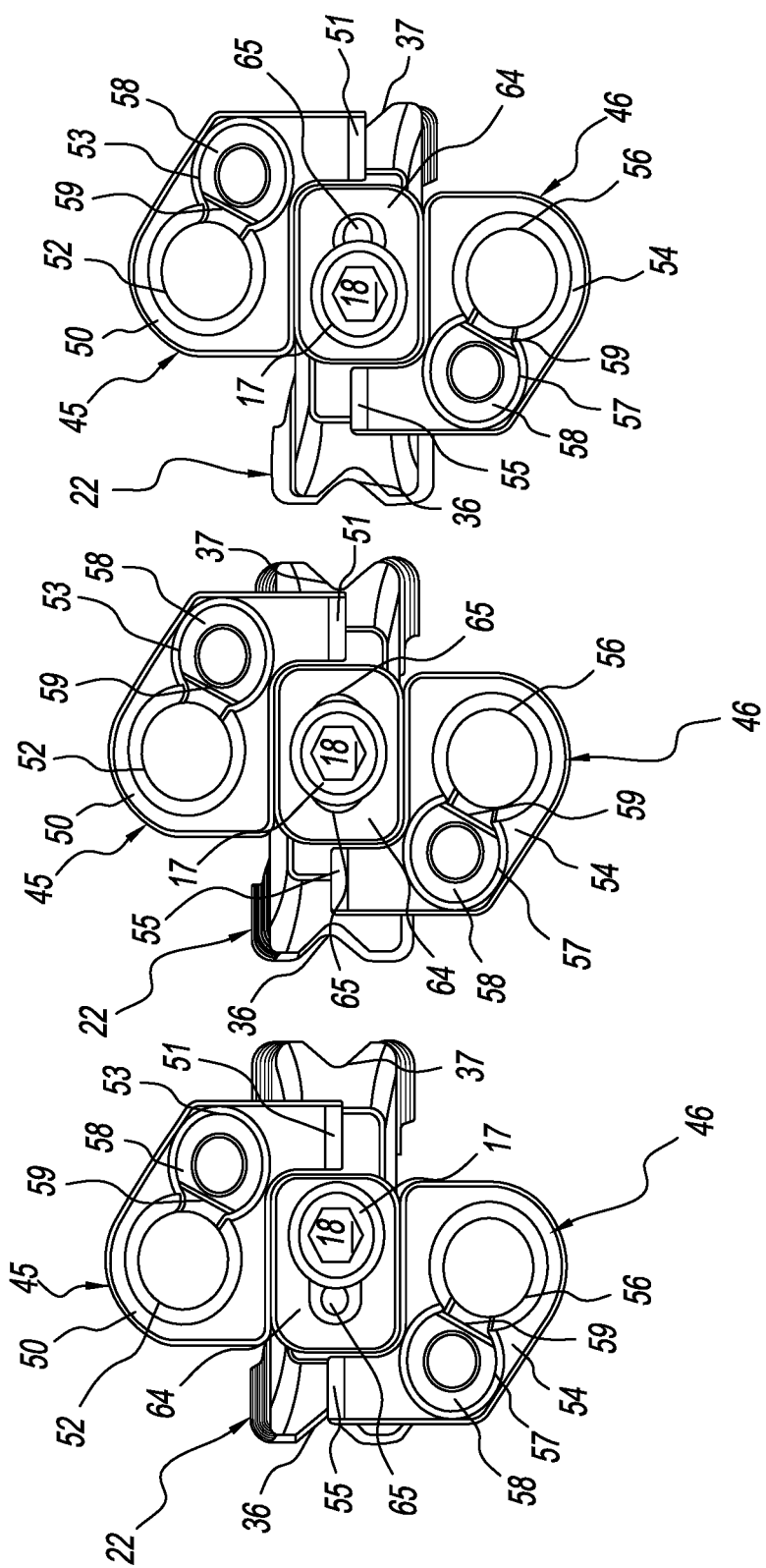
FIG. 6 is a series of end views of the lateral spinal interbody cage and lateral spine plate of FIG. 5 taken along line 6-6 thereof illustrating adjustability of the lateral spine plate relative to the lateral spinal interbody cage.
Figure 7:
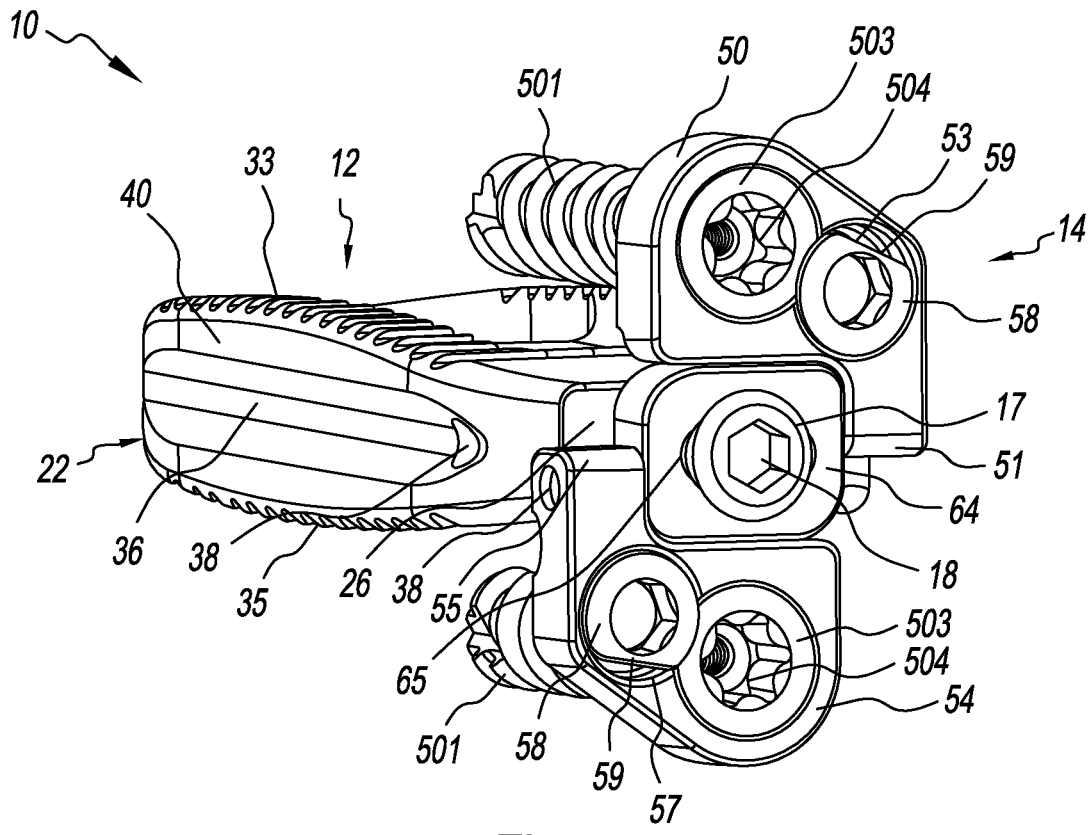
FIG. 7 is a rear side isometric view of the lateral spinal interbody cage and lateral spine plate of FIG. 1 with the vertebral attachment arms of the lateral spine plate in the extended or open position, bone screws received in each vertebral attachment arm and bone screw lock nuts in a locked position.

As depicted in FIG. 6, the bore 66 of the hub is preferably, but not necessarily, slotted to allow the threaded shaft 16 of the attachment pin 15 to translate anterior/posterior relative to the lateral interbody spine cage 12 so that position of the lateral spine plate 14 is not entirely dictated by placement of the lateral interbody spine cage 12. FIG. 6 depicts three positions of the lateral spine plate 14 relative to the lateral interbody cage 12 illustrating the anterior/posterior translation capability.

The lateral spine plate 14 is attached to a vertebra by two bone screws 500, one bone screw 500 for each vertebral attachment arm. A bone screw 500 is characterized by a head 503 having a socket 504 in the top. The socket 504 is configured for receipt of a like-configured instrument or tool (not shown) for driving/installing the bone screw 500. The bone screw 500 has a shank 501 with external threads/threading configured for receipt in a vertebral body. The threaded shank 501 terminates in a distal tip 502.

As indicated above, the first attachment arm 45 has a lock nut 58 disposed in the bore 53, and the second attachment arm 46 has a lock nut 58 disposed in the bore 57. The bore 53 of the first attachment arm 45 is adjacent the bone screw bore 52 as the lock nut 58 is used to prevent the bone screw 500 that is in the bone screw bore 52 from backing or coming out of the bone screw bore once the bone screw 500 has been received therein—therefore locking the bone screw 500 in the bone screw bore 52. The lock nut 58 has a round perimeter or rim with a flat, cutout or the like (flat) 59 along a portion thereof. The lock nut 58 is rotatable in the bore such that the flat 59 may be oriented in any rotational position. When the flat 59 is in a rotational position where the flat is adjacent the bone screw bore 52 (see FIG. 6), the bone screw bore 52 is "open" such that a bone screw head 17 is receivable in the bone screw bore 52. When the lock nut 58 is a rotational position wherein the flat 59 is not adjacent the bone screw bore, the perimeter/rim of the lock nut 58 partially covers the bone screw bore and thus the bone screw head 17 (see FIG. 7). The perimeter/rim of the lock nut also provides a cam function relative to the bone screw head in order to lock the bone screw 500 relative to the first attachment arm 46. The bore 57 of the second attachment arm 46 is adjacent the bone screw bore 57 as the lock nut 58 is used to prevent the bone screw 500 that is in the bone screw bore 57 from backing or coming out of the bone screw bore once the bone screw 500 has been received therein—therefore locking the bone screw 500 in the bone screw bore 52 in the same manner as described with respect to the first attachment arm 45.

Figure 8:
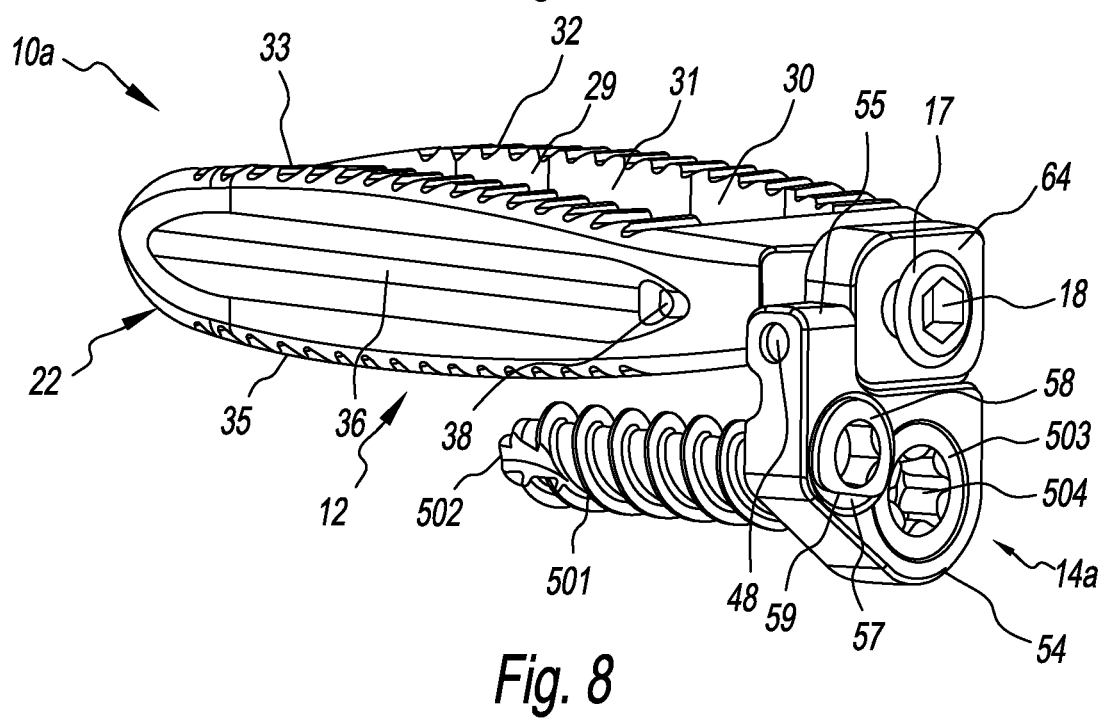
FIG. 8 is an isometric view of the lateral spinal interbody cage of FIG. 1 with a lateral spine plate having a single vertebral attachment arm with a bone screw received in the vertebral attachment arm and a bone screw lock nut in a locked position.

Referring to FIG. 8, there is depicted another exemplary form of a lateral spine plate, generally designated 14a, being a variation of the lateral spine plate 14, the lateral spine plate 14a shown connected to the lateral interbody spine cage 12 together forming a lateral spine implant 10a. The components, features, etc. of the lateral spine plate 14a that are the same as the lateral spine plate 14 have the same numbers as the lateral spine plate 14 while the those components, features, etc. that are different have the designation "a" after the number. The lateral spine plate 14a of FIG. 8 has a single vertebral attachment arm 54, here shown as the lower or inferior attachment arm 54, rather than the two vertebral attachment arms of the lateral spine plate 14.

Figure 10:
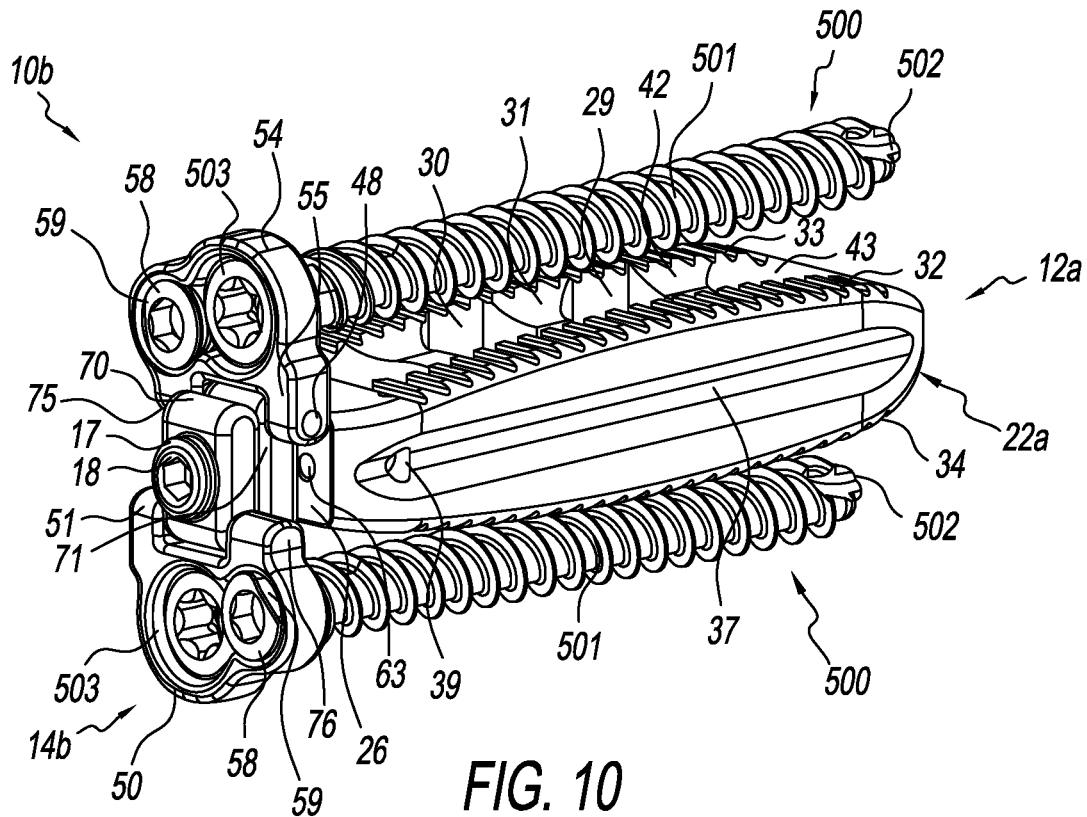
FIG. 10 is an isometric view of the lateral spinal interbody cage and lateral spine plate of FIG. 9, assembled via the attachment pin, with both vertebral attachment arms in the extended or open position, the bone screws received therein, and the bone screw nuts in the locked position.
Figure 11:
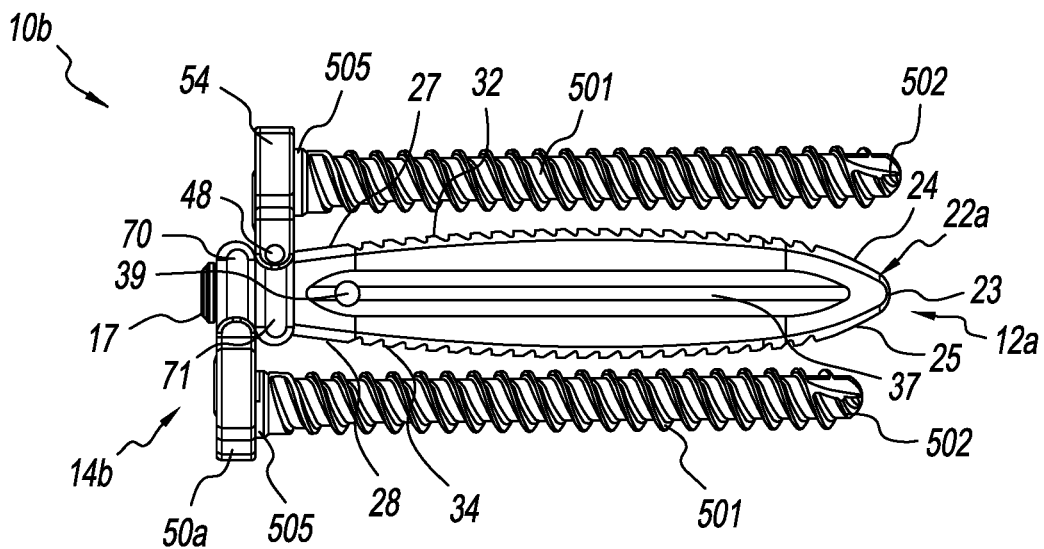
FIG. 11 is a side view of the lateral spinal interbody cage and lateral spine plate of FIG. 10.
Figure 12:
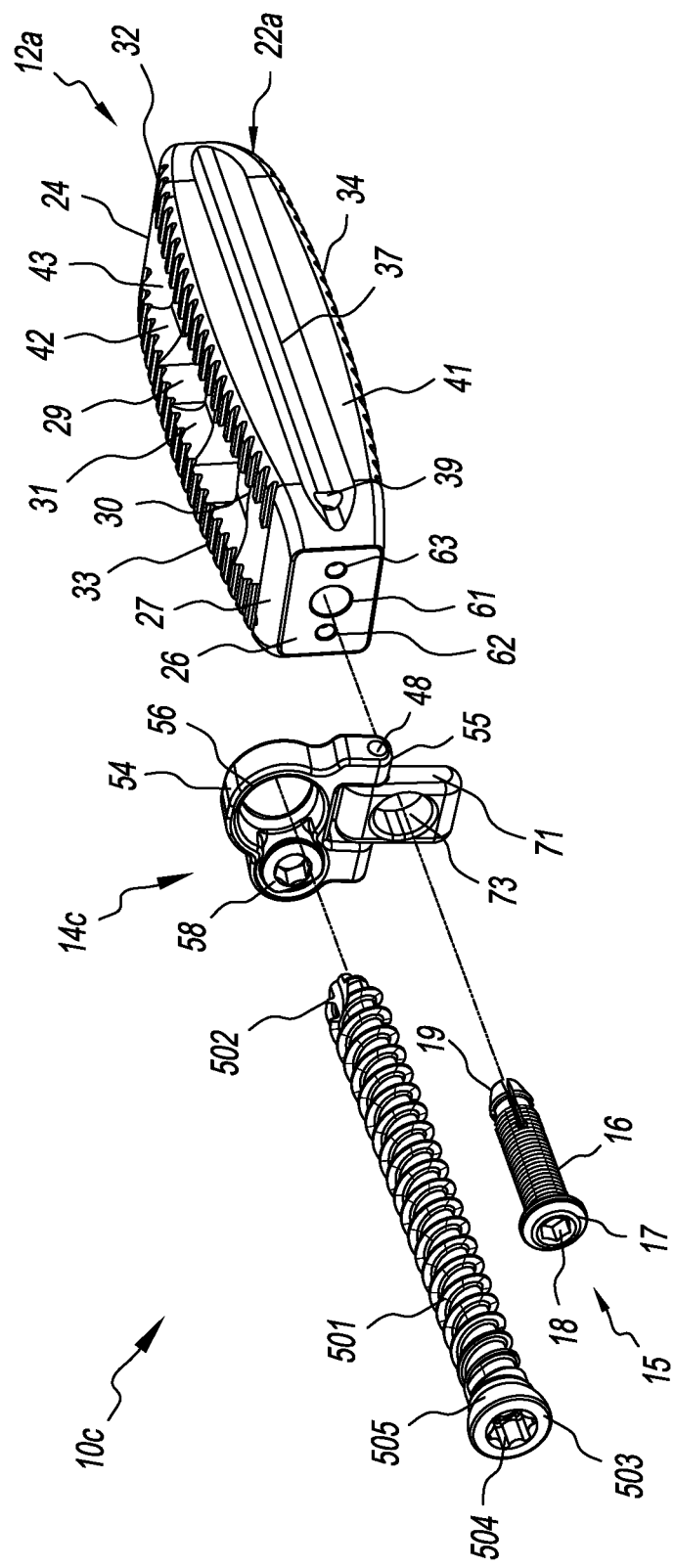
FIG. 12 is an exploded view of another lateral spinal interbody cage with a lateral spine plate having a single collapsible vertebral attachment arm fashioned in accordance with the principles of the present invention, the vertebral attachment arm in an expanded or open position and receiving a bone screw and attachment pin.
Figure 13:
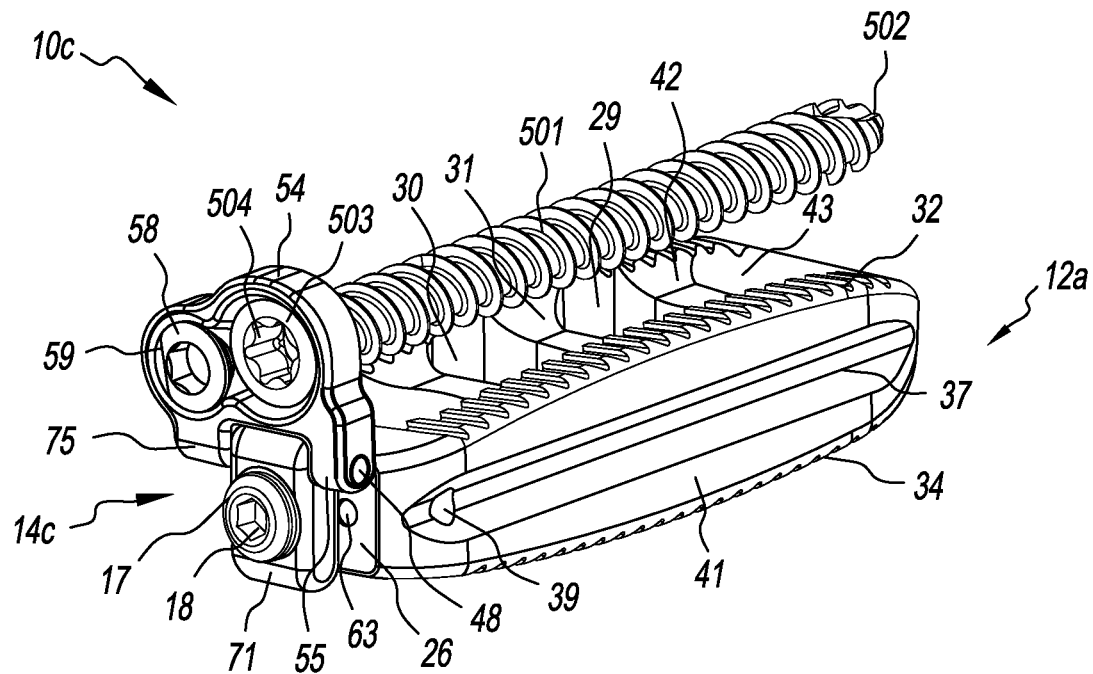
FIG. 13 is a rear side isometric view of the lateral spinal interbody cage and lateral spine plate of FIG. 12, assembled, with the bone screw received in the lateral spine plate and the bone screw nut in the locked position.
Figure 14:
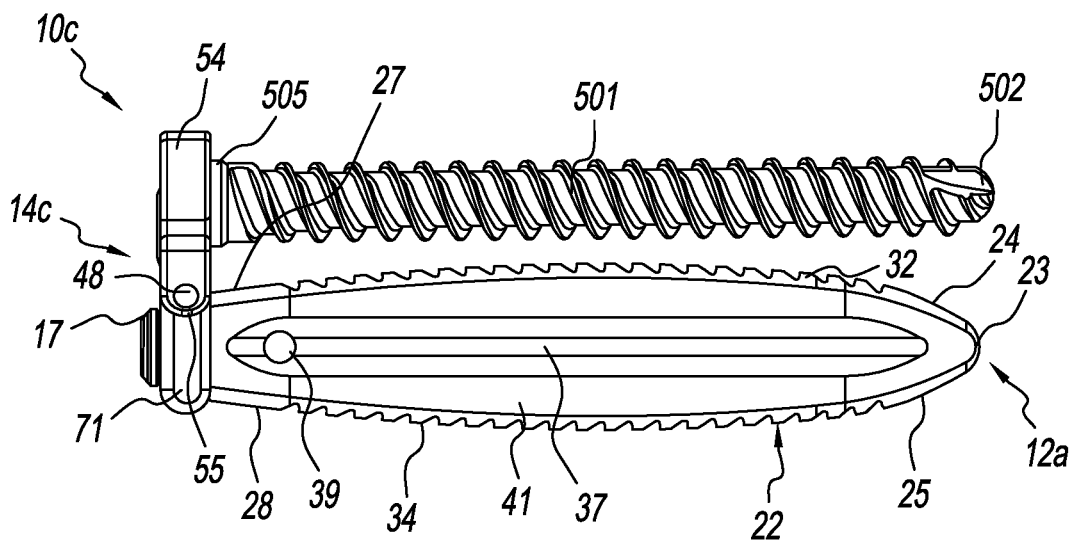
FIG. 14 is a side view of the lateral spinal interbody cage and lateral spine plate of FIG. 13.
Figure 15:
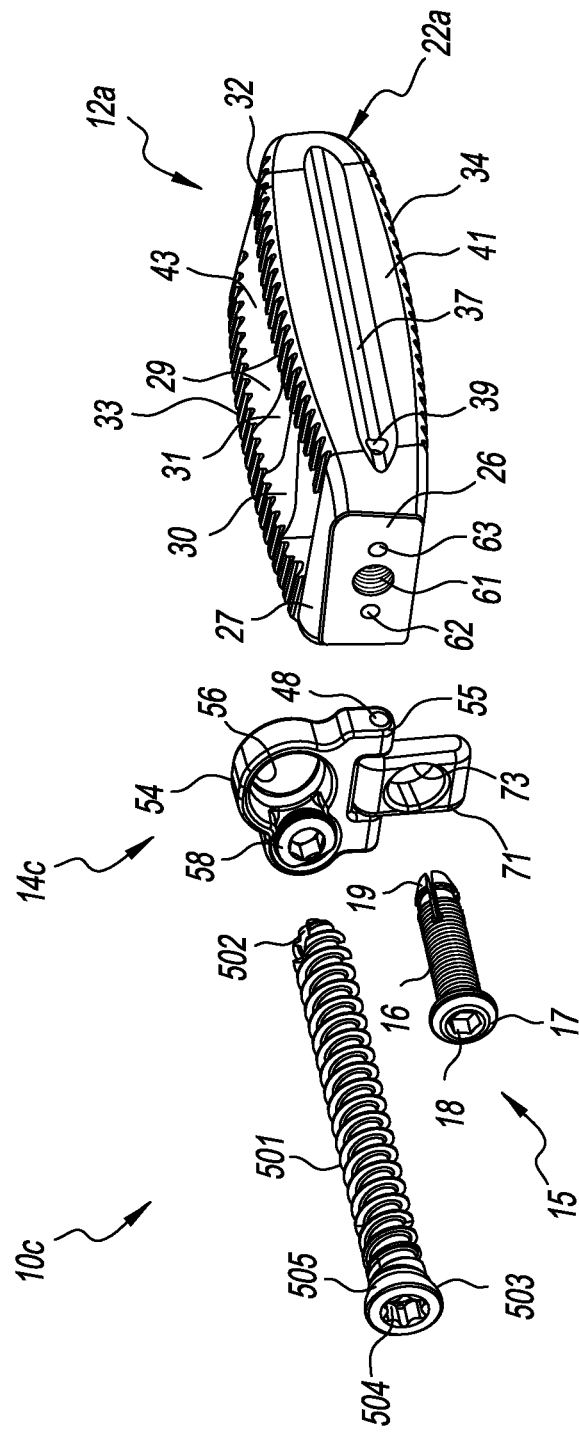
FIG. 15 is an exploded isometric rendering of the lateral spinal interbody cage and lateral spine plate of FIG. 12.
Figure 16:
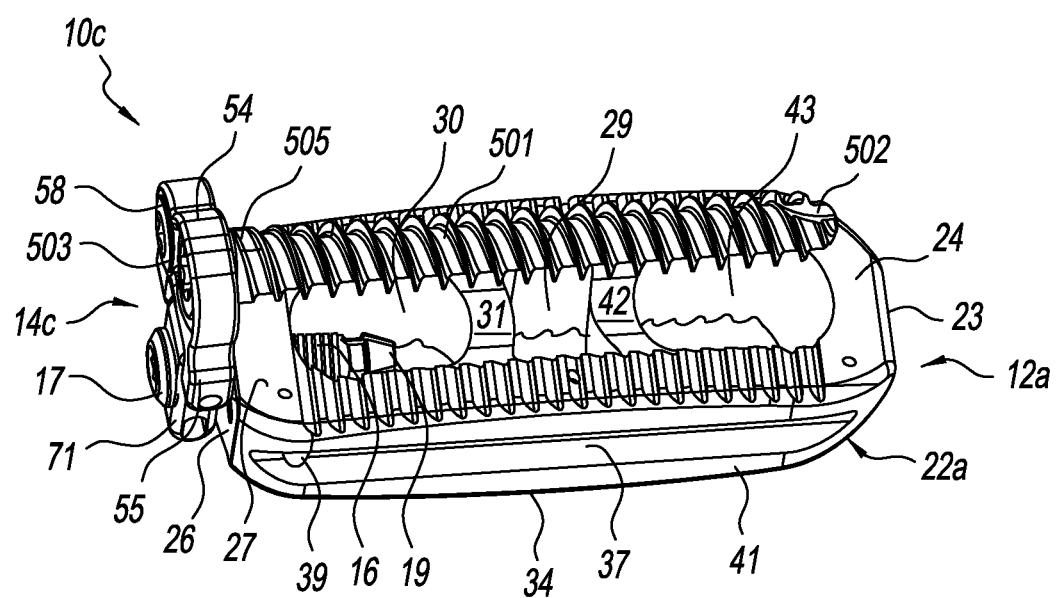
FIG. 16 is a top side rendering of the lateral spinal interbody cage and lateral spine plate of FIG. 12, assembled.

Referring to FIGS. 9-11, there is depicted another exemplary form of a lateral spine implant, generally designated 10b, having another exemplary form of a lateral interbody spine cage 12a and of a lateral spine plate 14b. The components, features, etc. of the lateral interbody spine cage 12a that are the same as the lateral interbody spine cage 12 have the same numbers as the lateral interbody spine cage 12 while the those components, features, etc. that are different have the designation "a" after the number. In like manner, the components, features, etc. of the lateral spine plate 14b that are the same as the lateral spine plate 14 have the same numbers as the lateral spine plate 14 while the those components, features, etc. that are different have the designation "b" after the number. FIG. 9 provides an exploded view of the components of the lateral spine implant 10b, namely the lateral interbody spine cage 12a, the lateral spine plate 14b, and the attachment pin 15, along with two bone screws 500.

The lateral interbody spine cage 12a differs from the lateral interbody spine cage 12 by having three rather than two cavities, namely a rear cavity 30, a middle cavity 29 separated from the rear cavity by a bridge 31, and a front cavity 43 separated from the middle cavity 29 by a bridge 42. Other components, features, etc. are the same.

The lateral spine plate 14b differs from the lateral spine plate 14 by the configuration of its hub and vertebral attachment arms. The lateral spine plate 14b has a hub defined by a first plate 70 having a central hole 72 and a second plate 71 having a central hole 73. The first and second plates 70, 71 are situated back-to-back such that the central holes 72, 73 align for reception of the attachment pin 15. The first (superior) attachment arm 46 has a first boss 55 on one lateral side thereof and a second lateral boss 75 on an opposite lateral side thereof. The hinge pin 48 extends through an upper portion of the first vertebral attachment arm 46 and the first and second lateral bosses 55, 75 to pivotally connect the first vertebral attachment arm 46 to the second plate 71. The second (inferior) attachment arm 45 has a first boss 51 on one lateral side thereof and a second lateral boss 76 on an opposite lateral side thereof. The hinge pin (not seen) extends through a lower portion of the second vertebral attachment arm 45 and the first and second lateral bosses 51, 76 to pivotally connect the second vertebral attachment arm 45 to the first plate 70. The first and second vertebral attachment arm 46, 45 can pivot/swing into and from a collapsed or closed position from and into an expanded or open position.

Referring to FIGS. 12-16 there is depicted another exemplary lateral spine plate, generally designated 14c, being a variation of the lateral spine plate 14b, the lateral spine plate 14c shown connected to the lateral interbody spine cage 12a together forming a lateral spine implant 10c. The components, features, etc. of the lateral spine plate 14c that are the same as the lateral spine plate 14b have the same numbers as the lateral spine plate 14b while the those components, features, etc. that are different have the designation "c" after the number. The lateral spine plate 14c of FIGS. 12-16 has a single vertebral attachment arm 54 connected to a single hub plate 71, here shown as the upper or superior vertebral attachment arm 54, rather than the two vertebral attachment arms of the lateral spine plate 14b.

Figure 17:
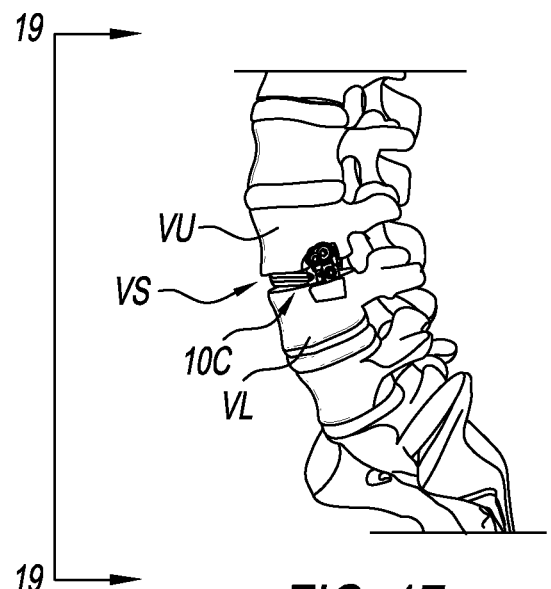
FIG. 17 is an isometric side rendering of a portion of a human spine with the lateral spinal interbody cage of FIGS. 12-16 implanted into the interbody space between upper and lower vertebrae with the lateral spine plate of FIGS. 12-16 attached to the upper vertebra.
Figure 18:
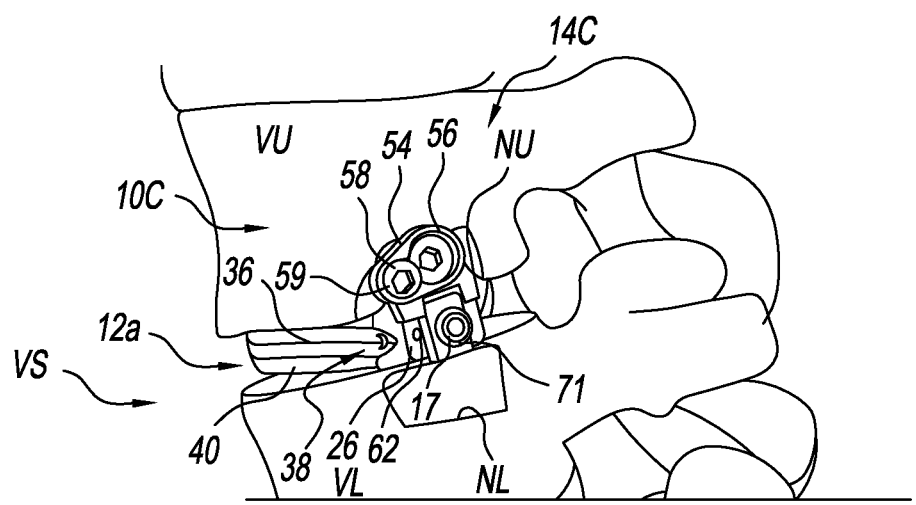
FIG. 18 is an enlarged side view of FIG. 17.
Figure 19:
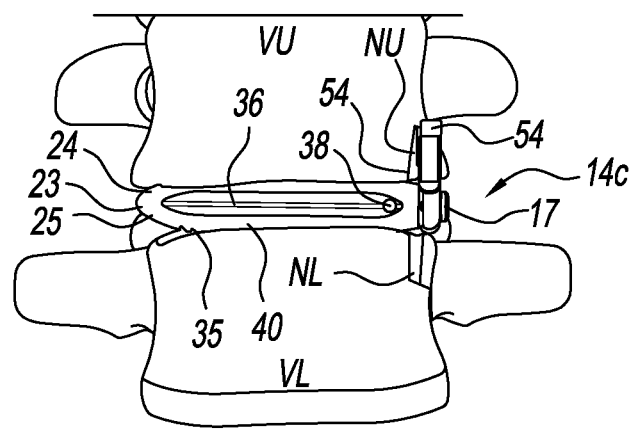
FIG. 19 is a front view of the portion of the spine of FIG. 17 taken along line 19-19 of FIG. 17.

FIGS. 17-19 show a lumbar portion of a human spine wherein the lateral spine implant 10c with the lateral spine plate 14c attached to the lateral interbody cage 12a has been implanted/installed in the vertebral space VS. The vertebral attachment arm 54 has been attached to the upper (superior) vertebra VU within an upper vertebral notch NU. A lower vertebral notch NL in the lower (inferior) vertebra VL is shown for a lower vertebral attachment arm of the lateral spine plate if desired.

It should be appreciated that dimensions of the components, structures, and/or features of the present lateral spine plate implant may be altered as desired within the scope of the present disclosure.

What is claimed is:

1. A lateral spine plate for attachment to a lateral side of a vertebra of a spine, the lateral spine plate comprising:
   a body having a front, a back, a top, a bottom, a first lateral side, a second lateral side, an axis defined from the front to the back, and a slot transverse to the axis and extending from proximate the first lateral side to proximate the second lateral side and through the body along the axis from the front to the back;
   a pivot post extending laterally outward from the first lateral side of the body;
   a connector situated in the body and extending rearwardly from the slot, the connector connected to the body and configured for attachment to an interbody spine implant; and
   an arm having a bore configured to receive and hold a bone screw for reception into a lateral side of a vertebra and pivotally connected to the pivot post so as to define a first pivot position wherein the bore is coaxial with the axis, and a second pivot position when the arm is pivoted relative to the body wherein the bore is positioned at the top of the body to allow the bone screw to be received into the lateral side of the vertebra, and a cam lock adjacent the bore to prevent egress of the bone screw received in the bore.

2. The lateral spine plate of claim 1, further comprising a second pivot post extending laterally outward from the second lateral side of the body, wherein the arm is further pivotally connected to the second pivot post.

3. The lateral spine plate of claim 1, further comprising:
   a second pivot post extending laterally outward from the second lateral side of the body;
   a second arm having a second bore configured to receive and hold a second bone screw for reception into the lateral side of a second vertebra and pivotally connected to the second pivot post so as to define a third pivot position wherein the second bore is coaxial with the axis, and a fourth pivot position when the second arm is pivoted relative to the body wherein the second bore is positioned at the bottom of the body to allow the second bone screw to be received into the lateral side of the second vertebra, and a second cam lock adjacent the second bore to prevent egress of the second bone screw received in the second bore.

4. The lateral spine plate of claim 1, wherein the connector has a threaded shaft configured to be received by the interbody spine implant.

5. The lateral spine plate of claim 4, wherein the connector further includes a resilient head.

6. A spine implant for attachment to an interbody spine implant and a lateral side of a vertebra of a spine, the spine implant comprising:
   a body having a front, a back, a top, a bottom, a first lateral side, a second lateral side, an axis defined from the front to the back, and a slot transverse to the axis and extending from proximate the first lateral side to proximate the second lateral side and through the body along the axis from the front to the back;
   a pivot post extending laterally outward from the first lateral side of the body;
   a pin situated in the body and extending rearwardly from the slot, the pin connected to the body and having external threading configured for attachment to a threaded hole of the interbody spine implant; and
   a plate having a hole configured to capture a bone screw for reception into a lateral side of a vertebra and pivotally connected to the body pivot post so as to define a first pivot position wherein the hole is coaxial with the axis, and a second pivot position when the plate is pivoted relative to the body wherein the hole is positioned at the top of the body to allow the bone screw to be received into the lateral side of the vertebra, and a cam lock mechanism adjacent the hole to prevent egress of a bone screw received in the hole.

7. The spine implant of claim 6, further comprising a second pivot post extending laterally outward from the second lateral side of the plate wherein the plate is further pivotally connected to the pivot post.

8. The spine implant of claim 6, further comprising:
a second pivot post extending laterally outward from the second lateral side of the body;
a second plate having a second hole configured to capture a second bone screw for reception into a lateral side of a second vertebra and pivotally connected to the second pivot post so as to define a third pivot position wherein the second hole is coaxial with the axis, and a fourth pivot position when the second plate is pivoted relative to the body wherein the second hole is positioned at the bottom of the body to allow the second bone screw to be received into the lateral side of the second vertebra, and a second cam lock mechanism adjacent the second hole to prevent egress of the second bone screw received in the second hole.

9. The spine implant of claim 6, wherein the pin further includes a resilient head.

\* \* \* \* \*